(12) United States Patent
Kaestle

(10) Patent No.: US 10,156,686 B2
(45) Date of Patent: Dec. 18, 2018

(54) DISPOSABLE SPO$_2$ GRIPS

(75) Inventor: Siegfried Kaestle, Nufringen (DE)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 358 days.

(21) Appl. No.: 13/320,549

(22) PCT Filed: May 4, 2010

(86) PCT No.: PCT/IB2010/051959
§ 371 (c)(1),
(2), (4) Date: Nov. 15, 2011

(87) PCT Pub. No.: WO2010/143083
PCT Pub. Date: Dec. 16, 2010

(65) Prior Publication Data
US 2012/0071740 A1 Mar. 22, 2012

Related U.S. Application Data

(60) Provisional application No. 61/185,216, filed on Jun. 9, 2009.

(51) Int. Cl.
*A61B 5/1455* (2006.01)
*G02B 6/38* (2006.01)
(Continued)

(52) U.S. Cl.
CPC ........ *G02B 6/3897* (2013.01); *A61B 5/14552* (2013.01); *A61B 5/6826* (2013.01); *A61B 5/6838* (2013.01); *G02B 6/0008* (2013.01)

(58) Field of Classification Search
USPC .................................... 600/310–344; 385/53
See application file for complete search history.

(56) References Cited

U.S. PATENT DOCUMENTS 4,964,826 A * 10/1990 Lobe ............................... 441/79
5,249,576 A 10/1993 Goldberger
(Continued)

FOREIGN PATENT DOCUMENTS

EP 0568380 A1 11/1993
EP 0898933 A2 3/1999
(Continued)

*Primary Examiner* — Eric Winakur
*Assistant Examiner* — Marjan Fardanesh

(57) ABSTRACT

When monitoring blood oxygen levels in a patient during a magnetic resonance scan, detachable and reusable fiber optic cable heads (16, 18, 98, 131, 132) are coupled to an SpO$_2$ monitor and to a hinged finger clip (40, 70, 90, 110, 190) on a patient. The finger clip (40, 70, 90, 110, 190) includes apertures (94, 196) and a retaining structure (44, 95, 198) to which a coupling portion of the fiber heads (16, 18, 98, 131, 132) are releasable attached. The retaining structure includes retaining clips (44, 198), slots (95), or the like that flexibly receive and align the fiber heads (16, 18, 98, 131, 132). The retaining structure (44, 95, 198) may be deformable, such that detachment of the fiber heads (16, 18, 98, 131, 132) at the end of the MR scan renders the finger clip (40, 70, 90, 110, 190) unusable to ensure that the clip is not reused, thereby preventing cross-infection between patients. Alternatively, the finger clip (40, 70, 90, 110, 190) may be reusable and the retaining clips may be designed to withstand repeated attachment and detachment of the fiber heads (16, 18, 98, 131, 132). A compressible foam or plastic layer is coupled to the interior of the clip portions to provide a snug fit. A transparent layer (54) attached to the foam or plastic layer permits light to pass through the foam/plastic aperture while preventing the fiber heads (16, 18, 98, 131, 132) from contacting the patient's skin.

14 Claims, 10 Drawing Sheets

(51) Int. Cl.
*A61B 5/00* (2006.01)
*F21V 8/00* (2006.01)

(56) References Cited

U.S. PATENT DOCUMENTS

| | | | |
|---|---|---|---|
| 5,273,041 A * | 12/1993 | Richards et al. | 600/411 |
| 5,337,386 A | 8/1994 | Noll et al. | |
| 5,348,003 A * | 9/1994 | Caro | 600/310 |
| 5,411,032 A | 5/1995 | Esseff | |
| 5,786,592 A | 7/1998 | Hok | |
| 6,026,312 A | 2/2000 | Shemwell et al. | |
| 6,041,247 A | 3/2000 | Weckstrom | |
| 6,321,100 B1 | 11/2001 | Parker | |
| 6,519,487 B1 * | 2/2003 | Parker | A61B 5/14552 600/310 |
| 6,671,531 B2 * | 12/2003 | Al-Ali et al. | 600/344 |
| 6,993,167 B1 | 1/2006 | Skladnev | |
| 2001/0002431 A1 | 5/2001 | Gurley | |
| 2006/0047190 A1 * | 3/2006 | Jenkins et al. | 600/340 |
| 2006/0053522 A1 | 3/2006 | Kimbell | |
| 2007/0244378 A1 | 10/2007 | Al-Ali et al. | |

FOREIGN PATENT DOCUMENTS

| | | |
|---|---|---|
| JP | 6014904 | 1/1994 |
| JP | 06014904 A | 1/1994 |
| JP | 9173322 | 7/1997 |
| WO | 03001180 A2 | 1/2003 |
| WO | 2004069046 A1 | 8/2004 |

* cited by examiner

DISPOSABLE SPO₂ GRIPS

CROSS REFERENCE TO RELATED APPLICATIONS

This application claims the benefit of U.S. provisional application Ser. No. 61/185,216 filed Jun. 9, 2009, which is incorporated herein by reference.

The present innovation finds application in magnetic resonance imaging (MRI) systems, particularly with regard to $SpO_2$ probes that are attached to a patient to monitor blood oxygen levels while the patient is positioned in an MRI device. However, it will be appreciated that the described techniques may also find application in other imaging systems, other magnetic resonance scenarios, other $SpO_2$ monitoring scenarios, and the like.

Conventional $SpO_2$ probes with electrical leads cannot be used in an MRI environment, since electrical cables and conductors can cause burns to a patient when currents are induced therein due to the high magnetic field generated in an MRI device. Therefore, oximetry probes for use during MRI scans typically employ fiber optic cables that guide light to the patient's limb or finger and back to the measurement electronics. The different kind probes offered vary in the way they can be attached to a patient's limb or finger. Multiple sizes of grips are provided to cover patients from neonates to adult. Special cables with alligator type of clips are available for quick and easy attachment.

However, conventional grips do not stick well to patient skin and do not fit all sizes of patients well, which can lead to measurement artifacts. Traditional clips do not fit smaller patients well. Reusable clips suffer from the risk of cross contamination because they are difficult to disinfect between patients.

Fiber optic probes are more expensive than electrical standard $SpO_2$ probes, thus preventing hospitals from maintaining a large range of sizes and attachment varieties to cover different patient sizes. In addition, some probe plugs require a tool to unscrew the fiber optic cable from the module, making it difficult to exchange a whole probe in between MR scans of different patients.

The present application provides new and improved systems and methods for monitoring blood oxygen levels in a patient using an $SpO_2$ probe with enhanced flexibility, which overcome the above-referenced problems and others.

In accordance with one aspect, an oximetry probe includes an appendage clip including first and second rigid clip portions. At least one of the clip portions includes a clip portion aperture on the exterior side of the clip portion, wherein the aperture releasably engages and aligns a fiber optic cable head through which light is transmitted into and/or received from an appendage received in the clip. The clip portion further includes a compressible foam or plastic layer affixed to the interior side of the clip portion, the compressible foam or plastic layer defining an aperture in alignment with the clip portion aperture, and an attachment structure that releasably attaches to a fiber optic cable head in alignment with the aperture.

In accordance with another aspect, a releasably attachable fiber optic oximetry probe for use with disposable appendage clips includes a pair of fiber optic cable heads that respectively transmit and receive light for monitoring blood oxygen levels in a patient, each fiber optic cable head having a coupling portion that releasably snaps into a respective retaining structure on an appendage clip that is attached to an appendage of a patient. The probe further includes a patient monitor that receives light from the fiber optic cable heads and determines a blood-oxygen level of the patient therefrom.

According to yet another aspect, a method measuring blood-oxygen content in a patient includes coupling one or more detachable fiber optic cable heads to respective flexible retaining structures on an appendage clip attached to an appendage of a patient, and coupling a fiber optic cable connected to the or more detachable fiber optic cable heads to a patient monitor. The method further includes emitting light from the patient monitor through the one or more detachable fiber optic cable heads, and receiving light from the one or more fiber optic cable heads. Additionally, the method includes monitoring a blood-oxygen level of the patient, removing the appendage clip from the patient, and detaching the one or more fiber optic cable heads from the appendage clip.

One advantage resides in the easy disconnection and reconnection of the fiber optic leads and the fiber optic heads, making the heads detachable.

Another advantage is that the $SpO_2$ probes can be color-coded according to size.

Another advantage resides in easy alignment of the finger and the clip.

A further advantage is that the leads pivot relative to the clip.

Other advantages include reduced cross-contamination between patients, simplified cleaning and disinfection, and disposability.

Still further advantages of the subject innovation will be appreciated by those of ordinary skill in the art upon reading and understand the following detailed description.

The drawings are only for purposes of illustrating various aspects and are not to be construed as limiting.

In accordance with various features described herein, detachable and rotatable fiber optic sensor heads (e.g., "fiber heads") are provided, which can be easily attached to and detached from different oximetry clips. The oximetry clips described herein may be disposable or reusable, and may be of several different sizes to accommodate the entire range of patient sizes, from premature neonatal patients through obese adults or adults suffering from a pituitary dysfunction such as gigantism. The described clips include a compressible foam or plastic layer that conforms to the patient appendage or finger, thereby providing additional fine-tuning of the fit to the patient. By making the fiber heads detachable, a health care facility or hospital need only keep one or a few sets of cables on hand. The disposability of the oximetry clips mitigates cross-infection among patients that might otherwise occur with reusable clips.

Figure 1:
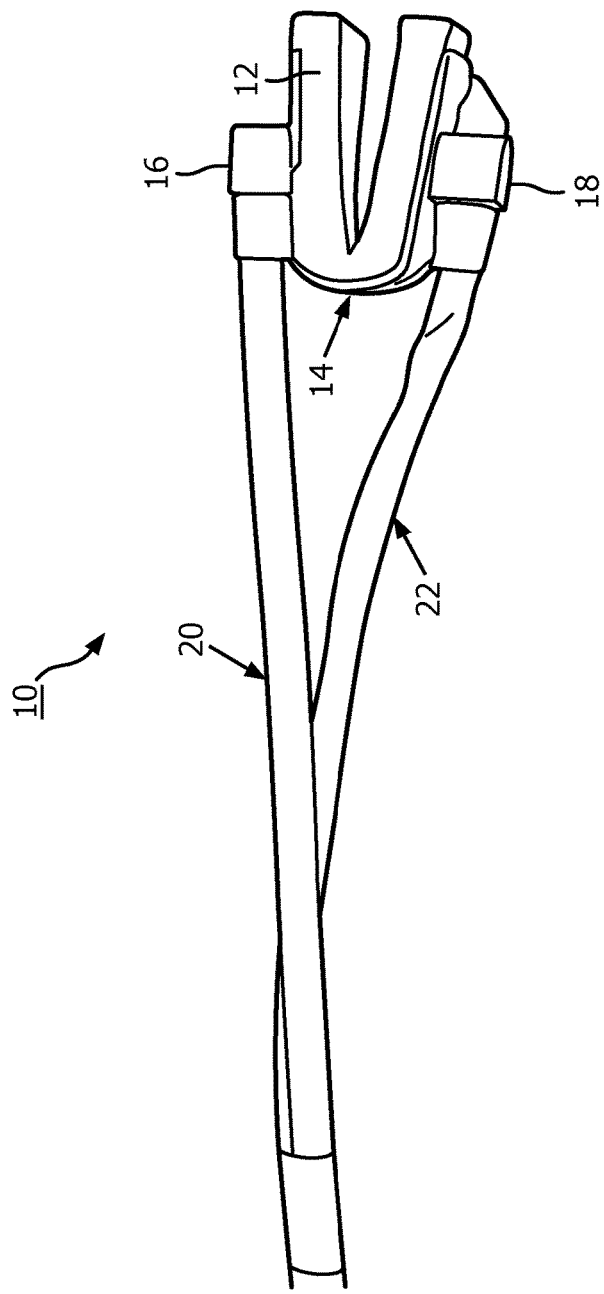
FIG. 1 illustrates a blood-oxygen level probe apparatus that includes a foam or plastic cushion coupled to an interior surface of a clip, which fits over a patient's finger.

FIG. 1 illustrates a blood-oxygen level probe apparatus 10 that includes a foam or plastic cushion layer 12 coupled to an interior surface of a clip 14, which fits over a patient's finger. A receiving fiber optic head 16, or "receiver," is coupled to a first side of the clip 14, and a transmitting fiber optic head 18, or "transmitter," is coupled to a second side of the clip. The receiver head 16 is coupled to a first fiber optic cable 20, while the transmitter head 18 is coupled to a second fiber optic cable 22. In this manner, flexible attachments are made to the fiber optics cables for $SpO_2$ measurement.

The interface between the transmitter and receiver heads and the clip is designed for easy and quick change of the attachment means (e.g., clips, grips, etc.). In one embodiment, the clip 14 is disposable (e.g., designed for single-use). In another embodiment, the foam or plastic layer 12 includes an adhesive material that couples the clip on the limb (e.g., finger) securely, as well as mitigates cross-infection.

The snap-in fiber heads 16, 18 provide for greater flexibility in selecting from a broad variety of clips of grips, which allows for quick insertion into the clips or grips and removal after use. Thus, the fiber optic cables can be reused with a number of disposable clips. The clip 14, which comes into contact with the patient, can be designed in various shapes and sizes to adapt to various limbs (e.g., fingers, toes, wrist, foot, ear, nose, forehead), and all patient sizes. In one embodiment, the reusable clips are alligator-like clips that attach to fingers and are provided different sizes.

The clip of FIG. 1, as well as the clips described herein in various other embodiments, may be contoured to the patient appendage (e.g., finger, toe, etc.) to which they are attached. This feature facilitates accurate positioning of the clip. Since the apertures to which the fiber heads are coupled are in a fixed position on the clip surfaces, the fiber heads are automatically aligned when they are snapped onto or otherwise affixed to the clip. When the clip is subsequently positioned on the patient appendage, the fiber heads are correctly positioned for blood-oxygen monitoring.

Figure 2:
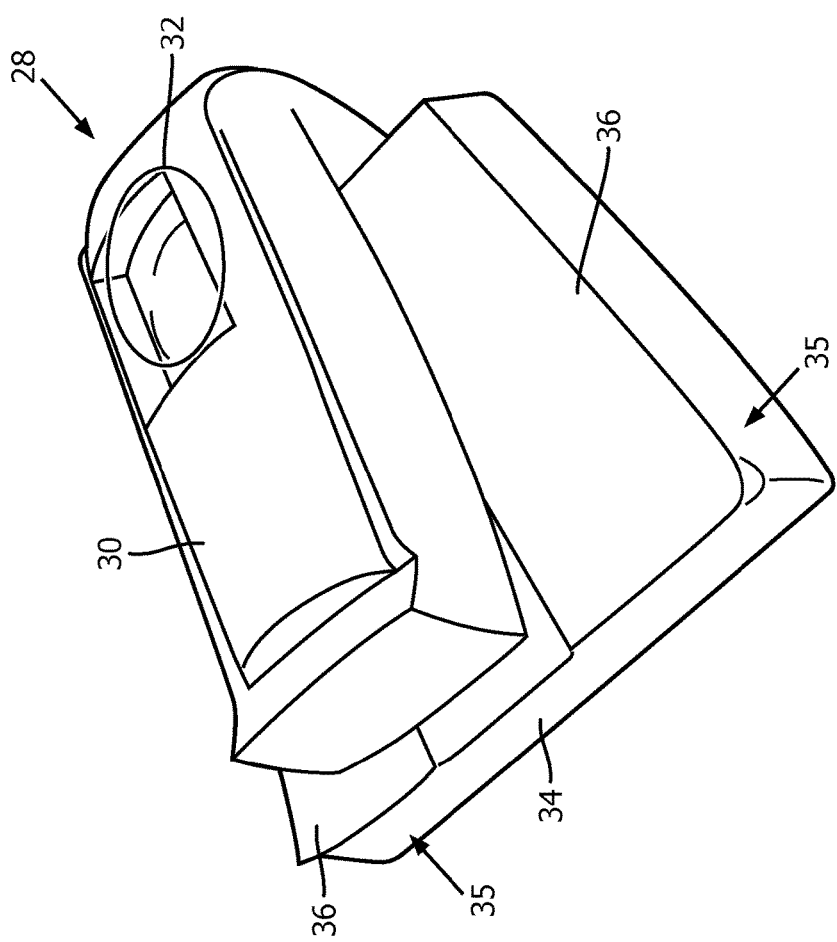
FIG. 2 illustrates a disposable clip having a rigid body with a fiber head receiving aperture.

FIG. 2 illustrates a disposable clip 28 having a rigid body 30 with a fiber head receiving aperture 32. A foam or soft plastic piece 34 is coupled to the clip, and may be constructed in several different ways. For instance, in the illustrated embodiment, the foam or plastic piece 34 has butterfly-like wings 35 that wrap around the side of the finger and have an adhesive layer 36 that sticks to the upper portion of the foam/plastic and/or clip and optionally the side of the finger. This embodiment is advantageous when the rigid body 30 is preformed to a cuff shape and has no hinge. In this case, the inner surface of the foam or plastic in contact with the top and bottom of a patient's finger is not covered with adhesive and the finger to be slipped in and out. When the front of the finger engages the front of the clip, fiber head receiving apertures are properly aligned to face each other and properly aligned across the finger tip (e.g., the fingernail) of the patient. An advantage of this construction is that ambient light from the side is prevented from entering the interior of the clip and interfering with the fiber optic light transmission and detection.

In one embodiment, foam or plastic pieces are pre-cut to fit the clip surface. Adhesive (e.g., medical transfer adhesive or the like) is applied to one or both sides of the foam or plastic piece. The adhesive on one side fixes the foam or plastic piece to the clip. The adhesive on the other side of the foam or plastic piece may be covered with a removable layer of material (e.g., a waxed paper or some other release liner), which is removed immediately prior to affixation of the clip to a patient appendage (e.g., finger, toe, etc.)

According to another embodiment, the foam (or plastic) pieces described herein are approximately 3-6 mm in thickness. Optionally, when foam (or plastic) pieces near the 3 mm end of the thickness range are used, a relatively stiff foam (or plastic) can be used, while a relatively softer and compressible foam (or plastic) can be used when the pieces are nearer the 6 mm thickness.

Figure 3:
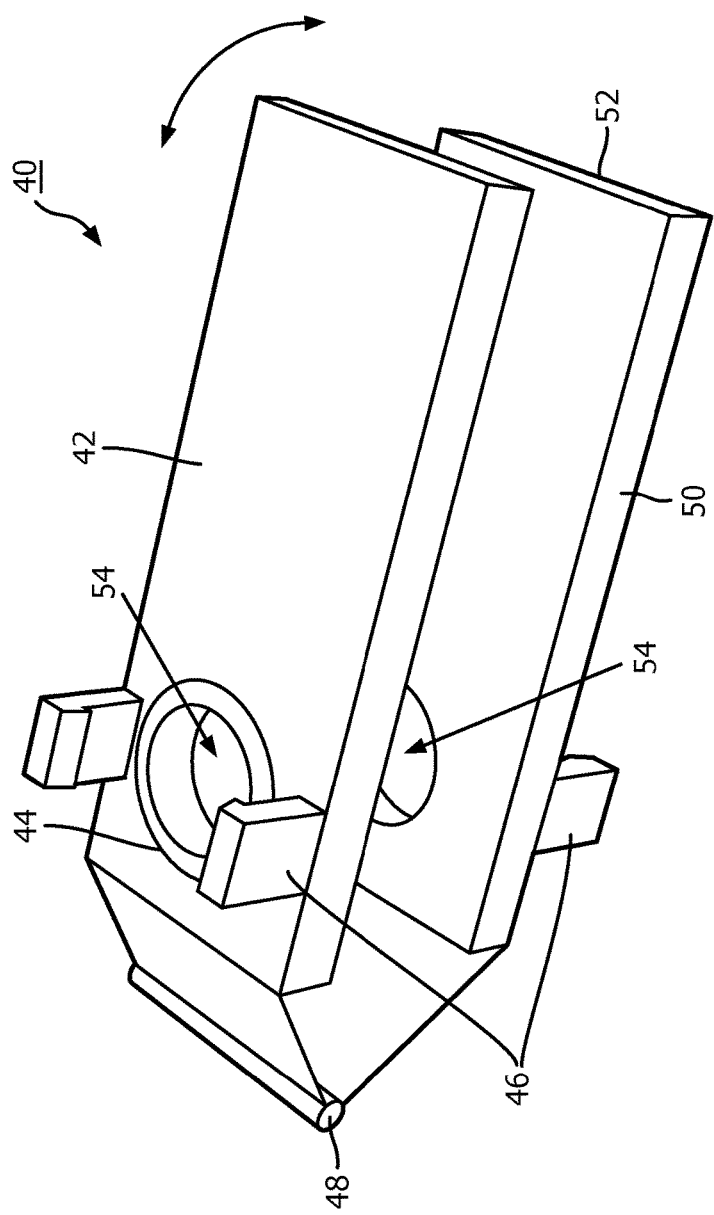
FIG. 3 illustrates a disposable clip that combines the ease of attachment and alignment of the fiber heads (e.g., transmitter and receiver) through the clip with the advantages of low-weight, comfort, secure fit, and low cost.

FIG. 3 illustrates a disposable clip 40 that combines the ease of attachment and alignment of the fiber heads (e.g., transmitter and receiver) through the clip with the advantages of low-weight, comfort, secure fit, and low cost. The clip 40 comprises a rigid, hard plastic body 42 that includes. The clip includes a window 44 for collecting or emitting light. Fiber head couplers 46 provide a snap feature for the fiber heads (not shown). A hinge 48 facilitates both easier application of a foam or plastic layer 50 and easier attachment to the finger. Optionally, the layer 50 is coated with an adhesive layer 52 that adheres to the patient's finger. A transparent plastic layer 54 seals the window 44 from the fiber head to protect it from being contaminated. The transparent layer 54 is in direct contact with the skin. This also mitigates a need for the fiber cross section to meet biocompatibility requirements.

In one embodiment, the foam or plastic layer is fitted to the rigid piece and forms a cushion. The foam or plastic layer is coated with the adhesive and is attached to the finger by folding the rigid piece with the hinge 48 around the finger. The clip 40 can be constructed in different sizes and shapes. The rigid body 42 can be constructed in different colors indicative of size and/or application. Additionally, the fiber heads can be snapped in either of two directions, with cable exiting towards the finger tips or towards the hand.

In another embodiment, a reusable clip such as an alligator clip, which consists of cleanable components, can be used instead of a disposable clip. In this example, the reusable clip includes similar snap-in couplers 46 for the fiber heads.

Figure 4:
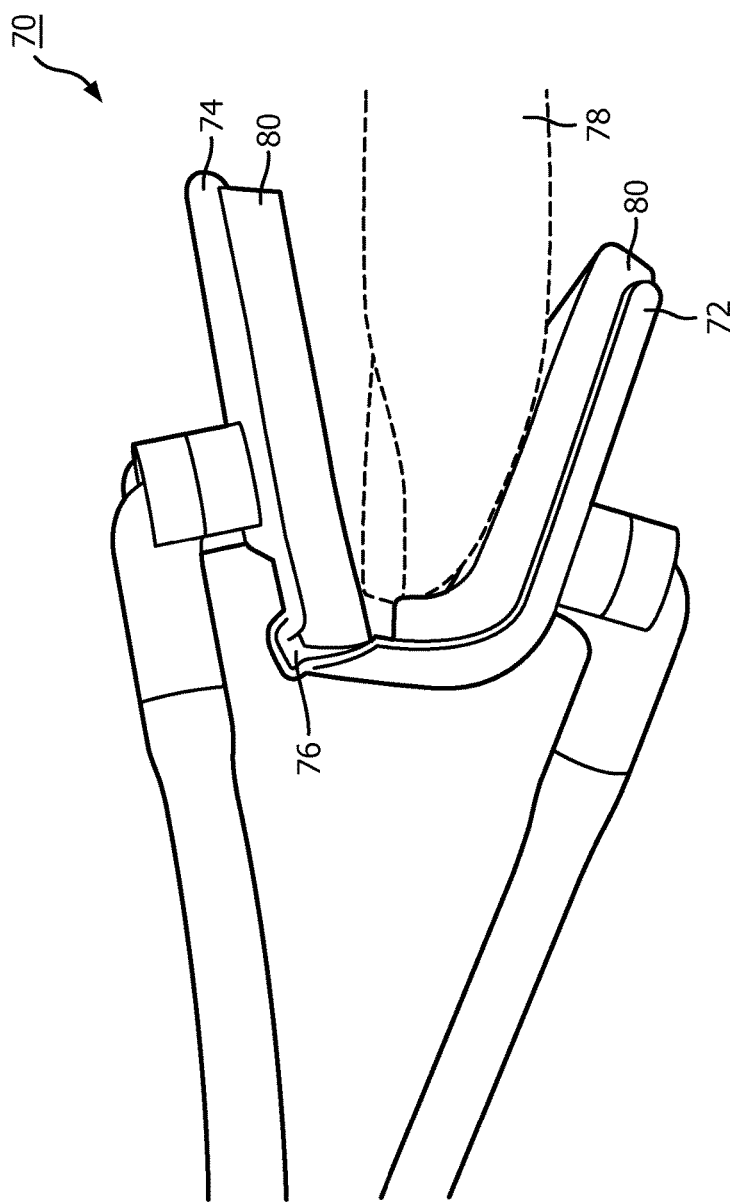
FIG. 4 illustrates an oximetry clip that includes a curved lower portion and a substantially linear or flat upper portion, coupled together by a hinge.

FIG. 4 illustrates an oximetry clip 70 that includes a curved lower portion 72 and a substantially linear or flat upper portion 74, coupled together by a hinge 76. The clip receives a patient's finger 78, and is closed thereabout. When the end of the finger engages the end of the curved lower portion 72, the clip and finger are aligned. A foam or soft plastic layer 80 is provided on the interior (e.g., finger side) of the upper and lower portions of the clip. Optionally, the foam or plastic layer is overlaid with an adhesive (not shown) that fixes the clip to the patient's finger. The foam or plastic is compressible to facilitate improved fit on the patient's finger. In this manner, a plurality of different sizes of clips can be provided, and a closest fit selected. The compressible foam or plastic layer then ensures that the selected clip provides a snug fit.

Figure 5:
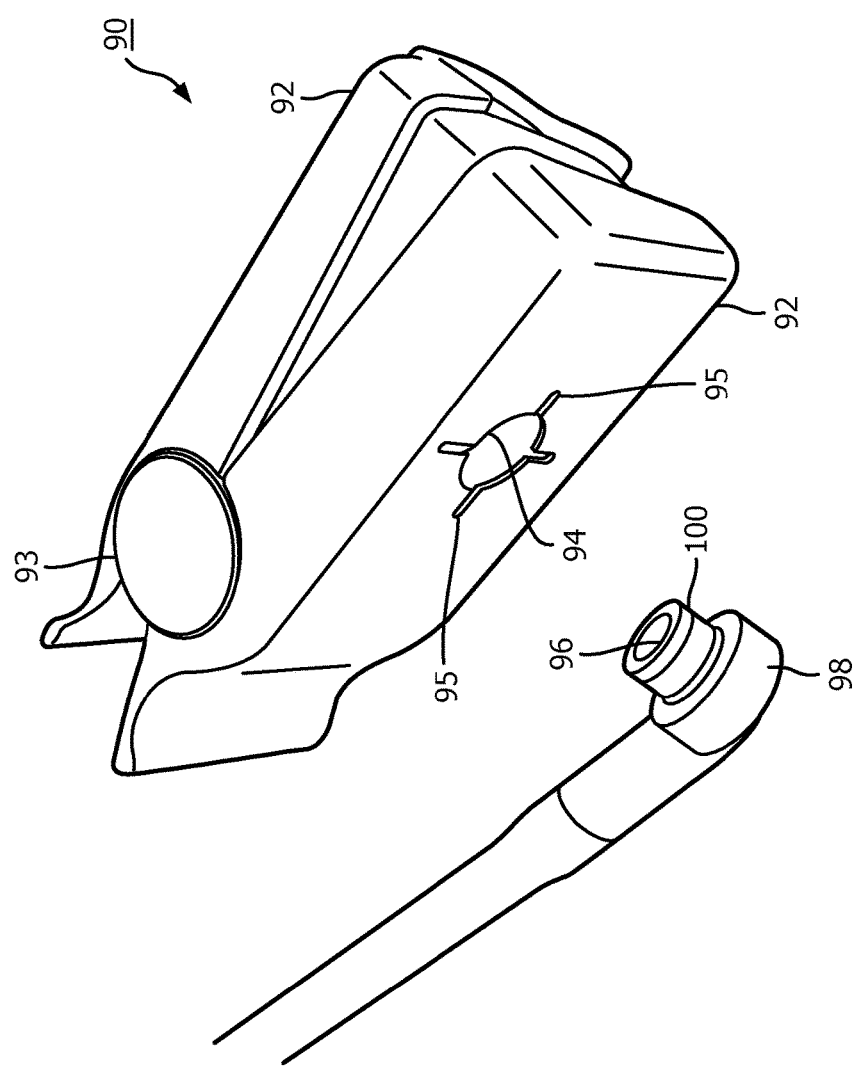
FIG. 5 illustrates an alligator-type blood-oxygen monitoring clip having first and second portions coupled together by a hinge.

FIG. 5 illustrates an alligator-type blood-oxygen monitoring clip 90 having first and second portions 92 coupled together by a hinge 93. A fiber head receiving aperture 94 receives a coupling portion 96 of a fiber head 98. The coupling portion has a truncated conical shape, the base of which forms a circular retaining "barb" 100 that releasably and rotatably engages the receiving aperture. In one embodiment, the receiving aperture 94 has grooves or slots 95 that extend radially outward from its circumference to provide a flexible, releasable, snug fit when mated to the coupling portion of the fiber head. The fiber head 98 is this removable attachable to the clip 90. The clip may be disposable or may be reusable (e.g., cleanable).

In another embodiment, coupling the fiber head to the disposable clip causes the receiving aperture to deform. Removal of the fiber head then causes permanent deformation of the receiving aperture and/or retaining structures positioned there around. For instance, the coupling portion of the fiber head may be made of a harder material than the clip into which the aperture is cut or stamped, and may include one or more barbs or projections, thereby permitting the coupling portion to be forced through the aperture to achieve a snug fit while requiring a greater force for removal. In another embodiment, the coupling portion has a truncated conical shape that snaps into retaining structures around the receiving aperture. Pulling the fiber head coupling portion back out of the aperture destroys the shape of the aperture so that a snug fit cannot again be achieved upon an attempt to reconnect the fiber head. This aspect ensures that the clip is not reused, thereby preventing cross-contamination between patients.

In another embodiment, the receiving aperture has a unique shape that complements the shape of the coupling portion of the fiber head so that the fiber head mates with the receiving aperture in a lock-and-key fashion. In this manner, the fiber head can be lockably attached to the clip. Optionally, the coupling portion includes a rotatable ring or the like that permits the fiber head to swivel 360° about the coupling portion while the coupling portion remains in a locked position. To further this example, the receiving aperture may include a one or more slots, and the coupling portion of the fiber head may include complementary projections that fit into the slots. The coupling portion may then be rotated (e.g., ⅛ turn. ⅙ turn, or some other amount) to lock into place.

Figure 6:
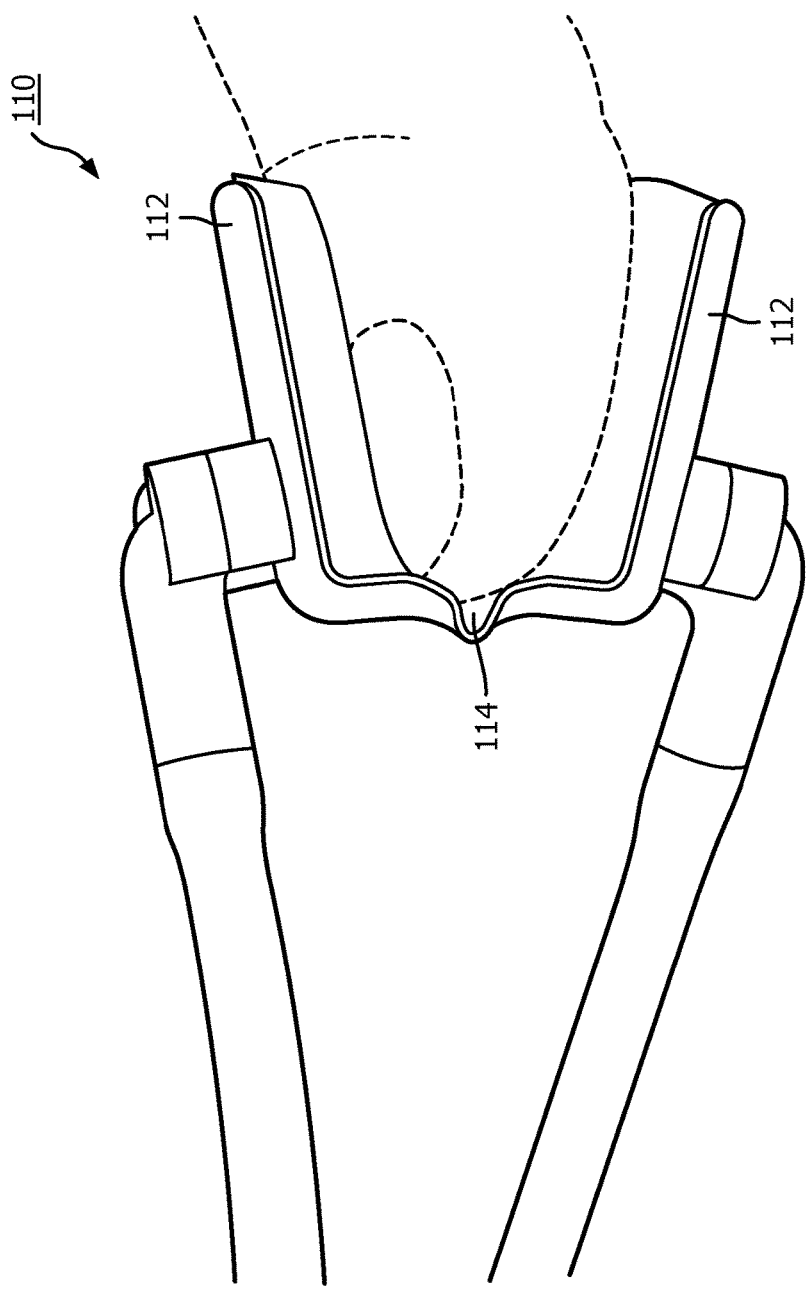
FIG. 6 illustrates a blood-oxygen level monitoring clip that includes first and second portions coupled together by a hinge.

FIG. 6 illustrates a blood-oxygen level monitoring clip 110 that includes first and second portions 112 coupled together by a hinge 114. The first and second portions 112 have similar or identical shape, thereby facilitating manufacture of the clip and permitting the clip to be applied to a patient's finger in opposite orientations without affecting function.

Figure 7:
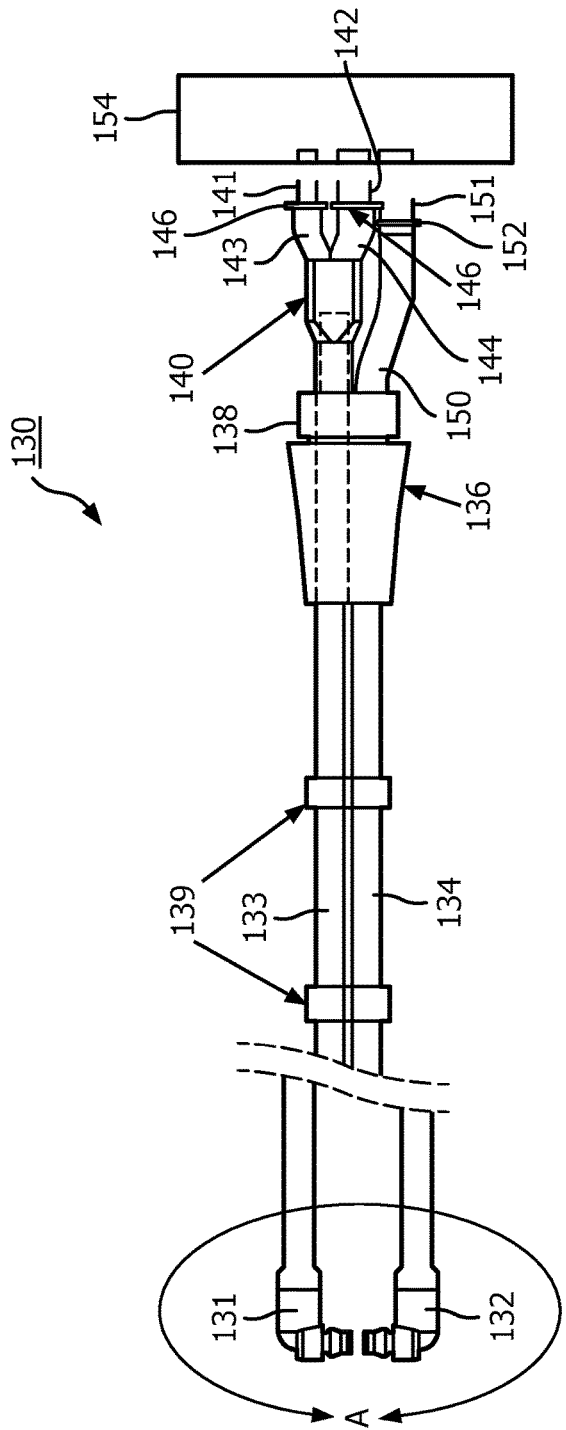
FIG. 7 illustrates an $SpO_2$ monitoring probe that includes first and second fiber heads (e.g., a receiver head and a transmitter head), shown in "Detail A," which is delineated by a circle with an "A."

FIG. 7 illustrates an SpO₂ monitoring probe 130 that includes first and second fiber heads 131, 132 for snap connection with one of the clips (e.g., a receiver head and a transmitter head), shown in "Detail A," which is delineated by a circle with an "A." Each fiber head is coupled to a fiber optic cable 133, 134 near the patient end of the probe. The cables 133, 134 are passed through a boot 136 that is slidable over a sheath 138 that holds the cables together at a monitor end of the probe, and may be coupled together at one or more points using a heat-shrink material 139. One of the cables is passed through a bifurcation block 140 that divides the fibers therein into two fiber bundles 141, 142 that are passed through respective sheaths 143, 144 and end pieces 146, 148. The other cable continues through its sheath 150, and the fiber bundle 151 therein exits through another end piece 152. The fiber bundles are coupled to a patient monitor 154 that sends red and/or IR light to and receives attenuated or reflected red and/or IR light carrying blood-oxygen measurement information and generates an output indicative of the blood-oxygen level.

According to an example the fiber bundle 141 is a 0.071-inch diameter (randomized) fiber bundle, and the fiber bundle 142 is a 0.122-inch diameter (randomized) fiber bundle. The end pieces 146, 148 are stainless steel end tips, each having an inner diameter of sufficient width to accommodate the fiber bundle passing through it. The fiber bundle 151 is a 0.141-inch diameter fiber bundle, and the end piece 152 is a stainless steel end tips having an inner diameter of sufficient width to accommodate the fiber bundle 151 passing through it. In this example, the sheath 143 is a 0.160-inch outer diameter silicone sheath, and the sheaths 144, 150 are 0.215-inch outer diameter silicone sheaths. It will be appreciated that the foregoing dimensions and materials are provided for illustrative purposes only, and that other dimensions and materials may be used in accordance with the herein-described features and embodiments.

Figure 8:
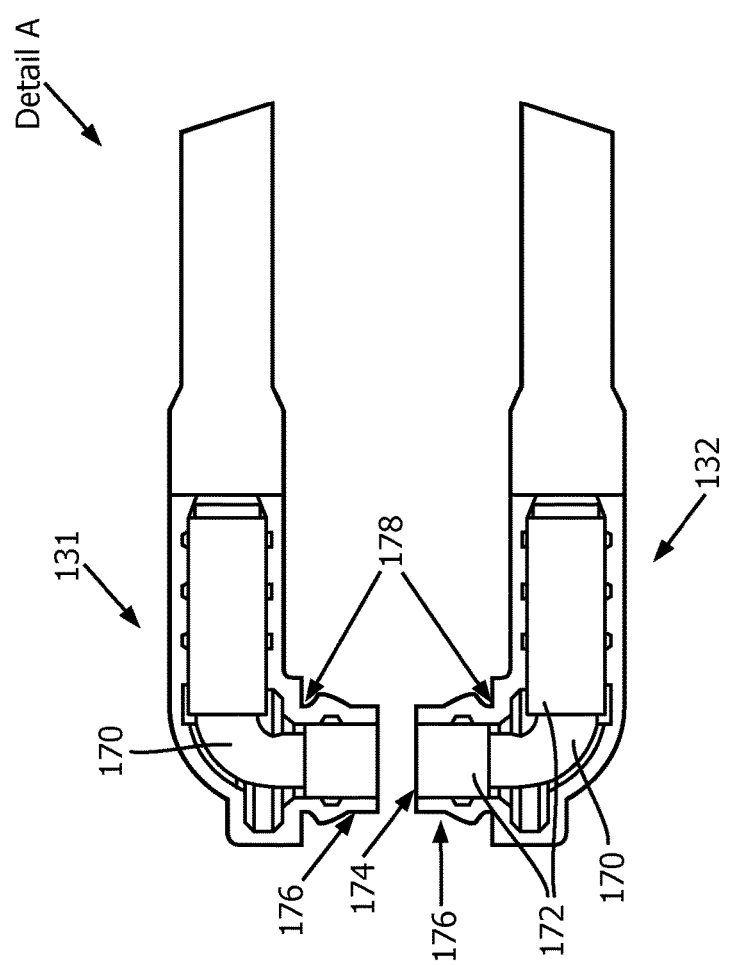
FIG. 8 is an enlarged view of "Detail A", showing the fiber heads in detail.

FIG. 8 is an enlarged view of "Detail A", showing the fiber heads 131, 132 in detail. Each fiber head includes a fiber bundle 170 that passes through a bushing 172. The end 174 of each fiber bundle is polished down until it is flush with the surface of a coupling portion 176 of the fiber head. The coupling portion includes a barb ring or lip 178 (shown in cross section) that releasably connects the fiber head to retaining structures around a receiving aperture in a finger clip or the like. In this manner, the fiber head can be releasably connected to multiple disposable clips.

In one embodiment, the fiber bundle 170 has a numerical aperture of 0.66 and a 4.0 mm diameter.

Figure 9:
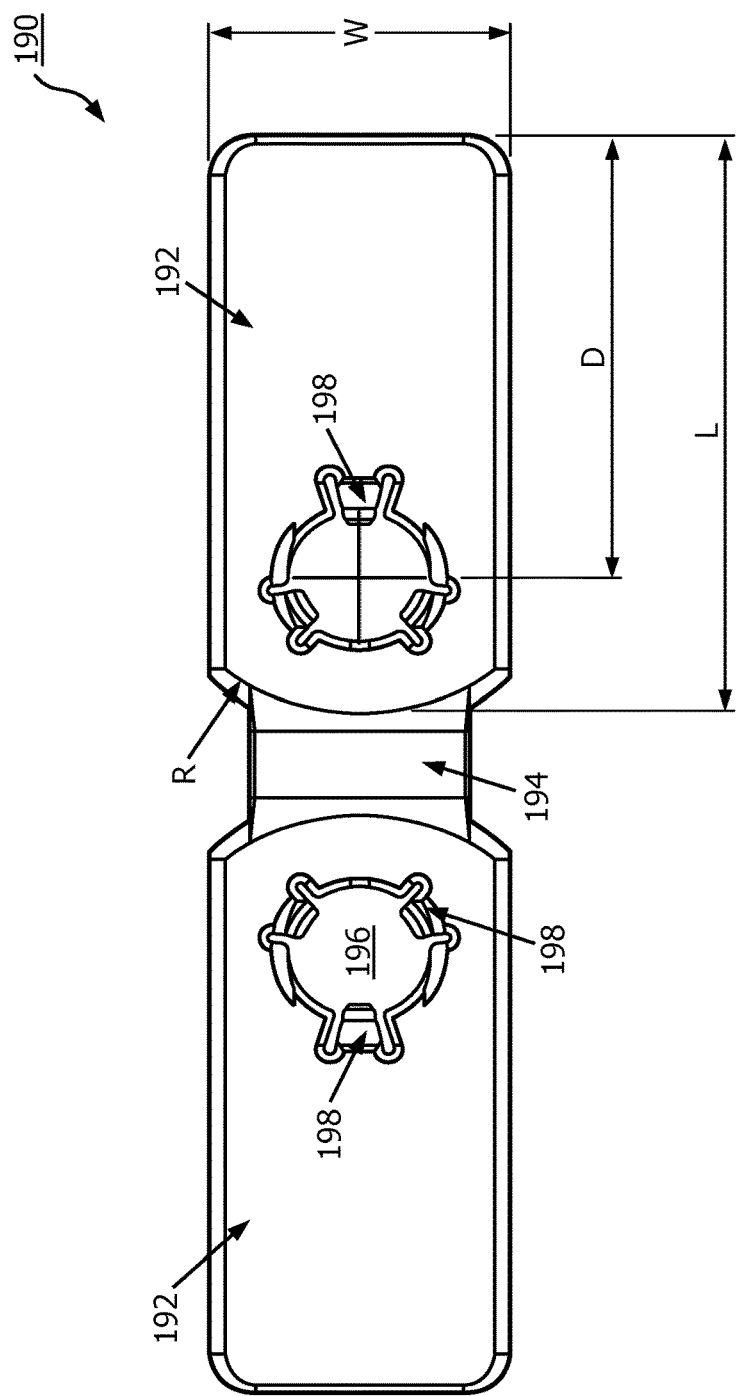
FIG. 9 illustrates a top-down view of an open disposable blood oximetry clip that includes first and second clip portions coupled together by a hinge.
Figure 10:
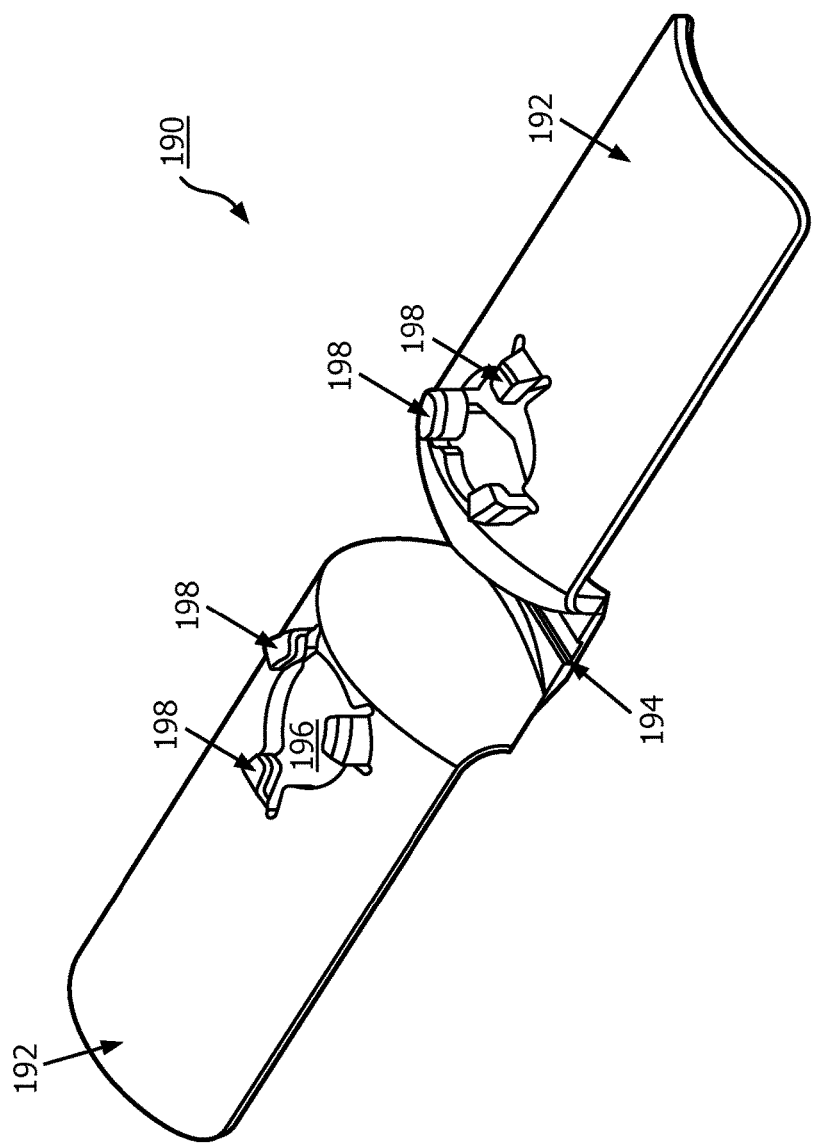
FIG. 10 illustrates an elevated perspective view of an open disposable blood oximetry clip that includes first and second clip portions coupled together by a hinge.

FIGS. 9 and 10 illustrate, respectively, a top-down view and an elevated perspective view of an open disposable blood oximetry clip 190 that includes first and second clip portions 192 coupled together by an integral hinge 194. The clip portions each have a receiving aperture 196 that receives a coupling portion (not shown in FIGS. 9 and 10) of a fiber head, as described herein. The perimeter of each receiving aperture has a plurality of integral flexible retaining clips 198 that lockably and removably receive and temporarily retain the coupling portion of the fiber head.

Dimensions of the clip 190 are labeled as a width W, a length L, a radius of curvature R (at a distal end of the clip), and a distance D from the center of the receiving aperture to the proximal end of the clip. In one embodiment, the length L is approximately twice the width W of the clip portion. The radius of curvature is approximately 0.5. The distance D is approximately ¾ of the distance from the proximal end of the clip portion to the distal end of the clip portion. The dimensions, of course, vary with the size of the finger or other appendage to be measured. Although the herein-described systems may be employed for any SpO₂ measurement application, they are particularly useful in an MR environment (e.g., in or near an MR device).

Having thus described the preferred embodiments, the invention is now claimed to be:

1. An oximetry probe, including:
   an appendage clip including first and second rigid clip portions, at least one of the clip portions including:
      a receiving aperture on an exterior surface of the clip portion, wherein the aperture releasably engages and aligns a fiber optic cable head through which light is transmitted into or received from an appendage received in the clip;
      a compressible foam or plastic layer affixed to an interior surface of the clip portion, the compressible foam or plastic layer defining an aperture in alignment with the clip portion aperture;
an attachment structure that releasably attaches to a fiber optic cable head in alignment with the aperture; and
wherein a portion of the exterior surface surrounding the receiving aperture permanently deforms upon removal of the fiber optic cable head from the receiving aperture, such that it is rendered nonfunctional, thereby ensuring that the appendage clip is not re-used;
wherein the fiber optic cable head comprises a coupling portion that has a truncated conical shape, a base of which forms a circular barb that snaps into the attachment structure and releasably locks the fiber optic cable head to the appendage clip, said coupling portion further including a rotatable ring adapted to permit the fiber optic cable head to swivel 360°.

2. The oximetry probe according to claim 1, further including:
a transparent window layer that acts as a barrier between a patient's skin and the fiber optic cable head and permits light to pass there through to or from the fiber optic cable head.

3. The oximetry probe according to claim 1, wherein the attachment structure includes:
one or more slots extending radially outward from the circumference of the receiving aperture, the slots permitting the receiving aperture to expand to accommodate the fiber optic cable head, and to releasably hold the fiber optic cable head in place.

4. The oximetry probe according to claim 1, wherein both the first and second rigid clip portions are substantially identical in shape and form, and wherein a hinge is coupled to distal ends thereof.

5. The oximetry probe according to claim 4, wherein the first and second rigid clip portions and the hinge are integrally molded plastic.

6. The oximetry probe according to claim 1, further including an adhesive layer that overlays the compressible foam or plastic layer.

7. The oximetry probe according to claim 1, wherein the appendage clip is color-coded to indicate size of the appendage clip.

8. The oximetry probe according to claim 1, wherein the oximetry probe is compatible with a magnetic resonance (MR) environment.

9. A releasably attachable fiber optic oximetry probe for use with disposable appendage clips, including:
a pair of fiber optic cable heads that respectively transmit and receive light for monitoring blood oxygen levels in a patient, each fiber optic cable head having a coupling portion that releasably snaps into a respective retaining structure on an exterior surface of an appendage clip that is attached to an appendage of a patient;
a patient monitor that receives light from the fiber optic cable heads and determines a blood-oxygen level of the patient therefrom; and
wherein the removal of the coupling portion causes the retaining structure of the exterior surface to further permanently deform to a point where it is non-functional for retaining the coupling portion such that the appendage clip is not reusable;
wherein each fiber optic cable head comprises a coupling portion that has a truncated conical shape, a base of which forms a circular barb that snaps into the attachment structure and releasably locks the fiber optic cable head to the appendage clip, said coupling portion further including a rotatable ring adapted to permit the fiber optic cable head to swivel 360°.

10. The oximetry probe according to claim 9, wherein the coupling portion has a truncated conical shape that snaps into, and is aligned by, the retaining structure, causing the retaining structure to deform to accommodate the coupling portion.

11. The oximetry probe according to claim 9, wherein the coupling portion is circular such that the fiber optic cable heads are rotatable while attached to the appendage clip.

12. The oximetry probe according to claim 9, wherein the oximetry probe is compatible with a magnetic resonance imaging environment.

13. A method of measuring blood-oxygen content in a patient, including:
coupling one or more detachable fiber optic cable heads to respective flexible retaining structures on corresponding exterior surfaces of an appendage clip attached to an appendage of a patient;
coupling a fiber optic cable connected to the one or more detachable fiber optic cable heads to a patient monitor;
emitting light from the patient monitor through the one or more detachable fiber optic cable heads;
receiving light from the one or more fiber optic cable heads;
monitoring a blood-oxygen level of the patient;
removing the appendage clip from the patient;
detaching the one or more fiber optic cable heads from the appendage clip; and
wherein the flexible retaining structures of the exterior surfaces are permanently deformed upon detachment of the one or more fiber optic cable heads, rendering the appendage clip unsuitable for subsequent use;
wherein each fiber optic cable head comprises a coupling portion that has a truncated conical shape, a base of which forms a circular barb that snaps into the attachment structure and releasably locks the fiber optic cable head to the appendage clip, said coupling portion further including a rotatable ring adapted to permit the fiber optic cable head to swivel 360°.

14. The method according to claim 13, performed in a magnetic resonance environment.

* * * * *